US009741102B2

(12) United States Patent
Cresens et al.

(10) Patent No.: US 9,741,102 B2
(45) Date of Patent: Aug. 22, 2017

(54) METHOD TO EVALUATE THE PRESENCE OF A SOURCE OF X-RAY BEAM INHOMOGENEITY DURING X-RAY EXPOSURE

(71) Applicant: Agfa HealthCare NV, Mortsel (BE)

(72) Inventors: Marc Cresens, Mortsel (BE); Herman Van Goubergen, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 328 days.

(21) Appl. No.: 14/402,363

(22) PCT Filed: Jun. 5, 2013

(86) PCT No.: PCT/EP2013/061591
§ 371 (c)(1),
(2) Date: Nov. 20, 2014

(87) PCT Pub. No.: WO2013/186099
PCT Pub. Date: Dec. 19, 2013

(65) Prior Publication Data
US 2015/0146959 A1    May 28, 2015

Related U.S. Application Data

(60) Provisional application No. 61/658,432, filed on Jun. 12, 2012.

(30) Foreign Application Priority Data

Jun. 11, 2012    (EP) .................................... 12171474

(51) Int. Cl.
*G06K 9/00*    (2006.01)
*G06T 5/00*    (2006.01)
(Continued)

(52) U.S. Cl.
CPC .............. *G06T 5/005* (2013.01); *A61B 6/582* (2013.01); *G01N 23/04* (2013.01); *G01N 23/046* (2013.01);
(Continued)

(58) Field of Classification Search
None
See application file for complete search history.

(56) References Cited

U.S. PATENT DOCUMENTS

2001/0033678 A1    10/2001    Hirai
2005/0094889 A1*    5/2005    Lin .......................... G06T 5/20
                                                                    382/261

(Continued)

FOREIGN PATENT DOCUMENTS

DE    10 2005 017 491 A1    10/2006
EP    2 050 395 A1    4/2009
EP    2 407 016 A1    1/2012
EP    2 477 153 A1    7/2012
JP    2000-070261 A    3/2000
WO    2007/043974 A1    4/2007

OTHER PUBLICATIONS

Official Communication issued in International Patent Application No. PCT/EP2013/061591, mailed on Aug. 8, 2013.

*Primary Examiner* — Manuchehr Rahmjoo
(74) *Attorney, Agent, or Firm* — Keating and Bennett, LLP (57) ABSTRACT

A statistical analysis is performed on pixel values of at least one region of interest in an image obtained by substantially uniform irradiation of an x-ray detector and deciding upon the presence of a source of x-ray beam in-homogeneity by comparing the results of the statistical analysis with at least one predetermined acceptance criterion.

16 Claims, 4 Drawing Sheets

(51) Int. Cl.
*H04N 5/32* (2006.01)
*G01T 7/00* (2006.01)
*G06T 7/00* (2017.01)
*G01N 23/04* (2006.01)
*G06T 5/40* (2006.01)
*G06T 7/80* (2017.01)
*H04N 5/365* (2011.01)
*A61B 6/00* (2006.01)

(52) U.S. Cl.
CPC .............. G01T 7/005 (2013.01); G06T 5/40 (2013.01); G06T 7/0012 (2013.01); G06T 7/80 (2017.01); H04N 5/32 (2013.01); A61B 6/40 (2013.01); *G06T 2207/10116* (2013.01); *G06T 2207/30004* (2013.01); *G06T 2207/30168* (2013.01); *H04N 5/3651* (2013.01)

(56) References Cited

U.S. PATENT DOCUMENTS

| | | | |
|---|---|---|---|
| 2006/0233305 A1 | 10/2006 | Hornig | |
| 2006/0262147 A1* | 11/2006 | Kimpe | G09G 3/20 345/690 |
| 2010/0098215 A1 | 4/2010 | Takahashi | |
| 2011/0057802 A1* | 3/2011 | Topfer | A61B 6/585 340/584 |
| 2013/0170627 A1* | 7/2013 | Topfer | A61B 6/585 378/207 |
| 2013/0182934 A1* | 7/2013 | Topfer | G06K 9/38 382/132 |

\* cited by examiner

METHOD TO EVALUATE THE PRESENCE OF A SOURCE OF X-RAY BEAM INHOMOGENEITY DURING X-RAY EXPOSURE

CROSS-REFERENCE TO RELATED APPLICATIONS

This application is a 371 National Stage Application of PCT/EP2013/061591, filed Jun. 5, 2013. This application claims the benefit of U.S. Provisional Application No. 61/658,432, filed Jun. 12, 2012, which is incorporated by reference herein in its entirety. In addition, this application claims the benefit of European Application No. 12171474.5, filed Jun. 11, 2012, which is also incorporated by reference herein in its entirety.

BACKGROUND OF THE INVENTION

1. Field of the Invention

The present invention relates to direct and computed radiography.

The invention more particularly relates to a method for preventing a sub-optimal gain map quality by detecting avoidable disturbances present in the x-ray beam-path during system (re)calibration.

2. Description of the Related Art

System calibration is extremely important for digital and computed projection radiography where flat-panel detectors and x-ray storage media in combination with digitizers are used to acquire digital images for clinical, veterinary or industrial use.

These image acquisition devices are rather complex hybrid (analog and digital) systems which are composed of a variety of highly interacting mechanical, electro-optical, physico-chemical, electronics, software and image-processing components and processes each having its typical tolerances and physical properties.

The overall image quality performance of a radiographic system can also depend on the ambient temperature, the humidity, the atmospheric pressure as well as on the x-ray exposure history linked to the degree of system usage and the system's actual age.

In addition gradually increasing levels of system contamination due to the external contact of the system components with radiographed patients, animals, objects, operator personnel or caused by fiber- and dust particle pollution can depend on the equipment's application-specific usage modes and the ambient climate conditions and can influence the properties and the behaviour of the system's individual components and processes thus leading to more frequent, beyond the periodically scheduled, cleaning and recalibration activities.

Especially for the flat-panel-detectors where next to dense pixel-individual light-trapping or direct x-ray detection array-circuitry also massive amounts of highly miniaturized pixel-, row-, and column-specific galvanic interconnections and several block-wise arranged read-out electronic circuits should cooperate harmonically the signal-quality and the x-ray response of the individual image-pixels, the image-rows and the image-columns will slowly or sometimes even suddenly degrade to a level where the required high image quality level can no longer be assured without corrective actions.

Therefore the image-acquisition system needs to be cleaned and recalibrated on a regular basis.

These activities are typically executed not only after the equipment is delivered and installed as a precondition to performing its initial acceptance test but also before each scheduled periodic quality control test.

After an equipment move, after system modifications and after preventive maintenance or repair interventions to critical system-components an additional system recalibration is often necessary as well to ensure a safe and effective operation of the radiographic image-acquisition system within the predetermined overall image quality range.

The system calibration process not only delivers a better adjusted and cleaner state of the radiographic equipment but also generates one or multiple image-wide maps at pixel resolution for the reconstruction of unstable and or defective pixels, rows and columns in addition to one or more gain maps for the software- or hardware-based, pixel-wise sensitivity-correction of raw diagnostic images. A gain map of a detector system is an image-wide representation of the (relative) signal response of each individual detector-pixel to x-ray dose.

Once established these freshly generated correction maps are used to optimize the image quality of each raw image acquired from then on and these maps will remain unchanged and in effect till the next system recalibration process, which will produce a new set of correction maps, is performed successfully.

In general several thousands of raw flat-panel-detector images acquired are corrected using the same set of correction maps, determined during the last system (re-)calibration.

(Re-)Calibration activities are, although of vital importance for a normal system operation, rather workflow-disturbing since the process of system-cleaning, equipment re-adjustments, calibration-dedicated image set acquisition and data-processing to generate the correction maps often requires the manual intervention of an operator and can be time-consuming while making a normal diagnostic use of the system impossible.

Without regulations or local recommendations on the minimum frequency of system recalibration the argument of the inevitable down-time due to system recalibration activities can lead to situations where users tend to postpone the system recalibration process as long as possible.

This by consequence means that even more than the normally already high amount of raw flat-panel-detector images acquired will be corrected based on that same set of correction-maps.

If the gain map, used for the pixel-wise sensitivity correction of the raw images acquired, would slowly degrade over time to a state where it becomes insufficiently representative, a vast amount of corrected diagnostic images might be impacted by various levels of image-artifacts of which some could be only faintly noticeable after a while and this might lead to deteriorated reading comfort, radiologist uncertainty and eventually to a false diagnosis.

Even an image-retake, causing a patient or object to be re-exposed in addition to introducing a time-costly workflow-disturbance, might in such cases still be insufficient to make up for the locally lacking, disturbed image quality of the corrected image since the same suboptimal gain map, the real cause of the problem, will again be used to correct the new image.

The gain map, which is determined as one of the outputs of the (re)calibration process, is often calculated from a set of non-x-ray exposed, raw dark-images in combination with a set of dedicated, homogeneously exposed raw flat field images.

Once the tube's focal spot, the source-to-image distance, the level of beam-collimation, the beam-filtration, the tube-voltage, the tube current and the exposure-time are set up and also the flat-panel-detector is geometrically positioned these dedicated image sets, required for the gain map determination during calibration, can easily be acquired sequentially from the operator's control cabinet without the need for further manual interventions to the system itself.

Sometimes though, visible objects that are forgotten to be removed (e.g. a dosimeter, a cleaning cloth, tools, all other kinds of objects commonly used by operators and service personnel during maintenance, repair and recalibration) as well as invisible objects (falsely positioned collimator blades, a badly mounted grid or automatic exposure control chamber) can still disturb the x-ray beam path during the actual acquisition of the calibration-dedicated images. These beam-path disturbance problems will not likely be seen from that remote operator location given that these individual images are acquired semi-automatically without any visual inspection performed on them at all.

These disturbing objects can be size-wise difficult to detect and can partially absorb the x-ray radiation towards the flat-panel detector-surface thus locally impacting the homogeneous character of the exposure field, required for the successful acquisition of the set of representative flat field images for the calculation of the gain map.

Disturbing objects can have various dimensions from very big (e.g. a screw-driver, a pull-over) to very small (e.g. a screw, a washer, a lost staple).

Some objects with a mixed material composition can locally introduce strongly fluctuating x-ray attenuation (e.g. a dosimeter) whereas others have hardly noticeable, fuzzy and noisy object-borders (e.g. a cleaning-cloth). Even an unexpected visit of an insect accidentally interfering with the x-ray beam path during system recalibration can't be totally excluded.

In addition non-corrected raw flat-panel detector images, also in scope for this inspection, can exhibit a significant level of streakiness and strip-wise signal-variation due to the multiple ASICs-based electronic circuits used for the parallel image read-out of the detector array.

An inspection concept relying on the signal difference between an object and its smooth background or on signal-gradient-based edge-analysis will be insufficiently effective to look for all these kinds of image-disturbances given the presence of the other non-object related noise sources inherent to raw, non-corrected images.

If no disturbing object inspection on each of the raw flat field exposed images is performed to upfront determine whether or not that image is sufficiently disturbance free and can be allowed to act as a valid and representative input image for the calculation of the gain map, sub-optimal gain maps for the correction of many thousands of future raw diagnostic images can potentially be generated without notice.

Best case such a sub-optimal gain map will generate a corrected verification flat field image, often acquired as a final step in the calibration procedure, which is showing a sufficient level of image disturbance to be regarded as a system calibration problem by the operator who is performing the (re)calibration activities.

In that case the calibration must be regarded as failed and a new calibration process with the acquisition of new flat field images is required.

Re-performing the system-calibration requires additional work and can significantly increase the system's down-time.

The problem originating from a disturbed gain map passes the calibration process undetected in case no final flat field verification, using the new but object-disturbed gain map for correction of the raw flat field image, is performed.

It will then depend on the radiologists experience and on the level of disturbance visibility whether or not that sub-optimal calibration state, generating disturbed diagnostic images after raw image correction, can be either detected and mitigated quickly by a system-recalibration or will inevitably lead to a reduced overall image quality level which might hamper the proper diagnoses of many corrected images to follow.

Although the fact that the acquisition of gain correction data should be done in the absence of any object in the X-ray beam irradiating the detector is well-known from prior art references EP 2 050 395: WO 2007/043974 and DE 10 2005 017491, none of the prior art references addresses the non-trivial problem with disturbing objects which may lead to imperceptible acquisition of corrupted gain correction data.

SUMMARY OF THE INVENTION

It is thus one aspect of this invention to provide a method to avoid acquisition of unacceptable gain correction data.

A similar problem with beam-path disturbing objects or surface-contamination arises for the highly demanding computed radiography applications too where gain maps to correct for the detector-specific, two-dimensional sensitivity-distributions of the x-ray storage detector-media are determined in manufacturing according to European patent application EP 2407016 A2 entitled "Method of determining the spatial response signature of a detector in computed radiography" and in co-pending European patent application 11151202.6 entitled "Method of removing the spatial response signature from a computed radiography image."

The above-mentioned aspects are obviated by a method having the specific steps set out below. Specific steps and features for preferred embodiments of the invention are also set out below.

This invention proposes a fast and effective method to prevent the above discussed problems caused by a disturbed gain map correction resulting from an insufficiently homogeneous x-ray beam state due to the presence of avoidable objects or surface contamination present anywhere in the beam-path during the system-(re)calibration activities.

An automatic method, relying on the statistical analysis of a multitude of adjacent or partially overlapping, potentially object-disturbed regions-of-interest, can act on the raw (non-corrected), dedicated flat field images, acquired for the purpose of gain map calculation to optimize the overall image quality performance of direct and computed radiography image-acquisition systems.

As a result a sub-optimal image condition can be detected and mitigated already early on in the process of gain map determination while performing an initial, periodic or additional system-(re)calibration.

Costly time-loss and unnecessary tube-wear associated with the operator-assisted acquisition of a set of beam-path disturbed, useless flat field images can thus be avoided and a higher certainty-level regarding the validity of the calculated gain map, an output of the (re)calibration process, can be achieved.

Further advantages and preferred embodiments of the present invention will become apparent from the following description and drawings.

DETAILED DESCRIPTION OF THE PREFERRED EMBODIMENTS

Upon an initial calibration after installation or while performing a periodic or an additional re-calibration of a flat panel detector direct radiography system, the use of this equipment for diagnostic imaging purposes is temporarily suspended.

Time and personnel are freed up to acquire new calibration-dedicated image sets, composed of non-exposed as well as homogeneously exposed raw flat panel detector images, and to be able to calculate the various updated defective pixel maps and updated gain maps, necessary to convert the many thousands of raw diagnostic images to follow into optimally corrected images.

Below a specific preferred embodiment of the method of detecting a sub-optimal gain-correction-map condition, caused by the acquisition of beam-path disturbed quasi homogeneously exposed images during system-calibration, is described for a flat panel detector radiography system where individual x-ray images, acquired to compose the set of homogeneously exposed images are individually subjected to a fast, automatic, disturbing object inspection method prior to being accepted as a valid input image for the calculation of an updated gain map.

Figure 1:
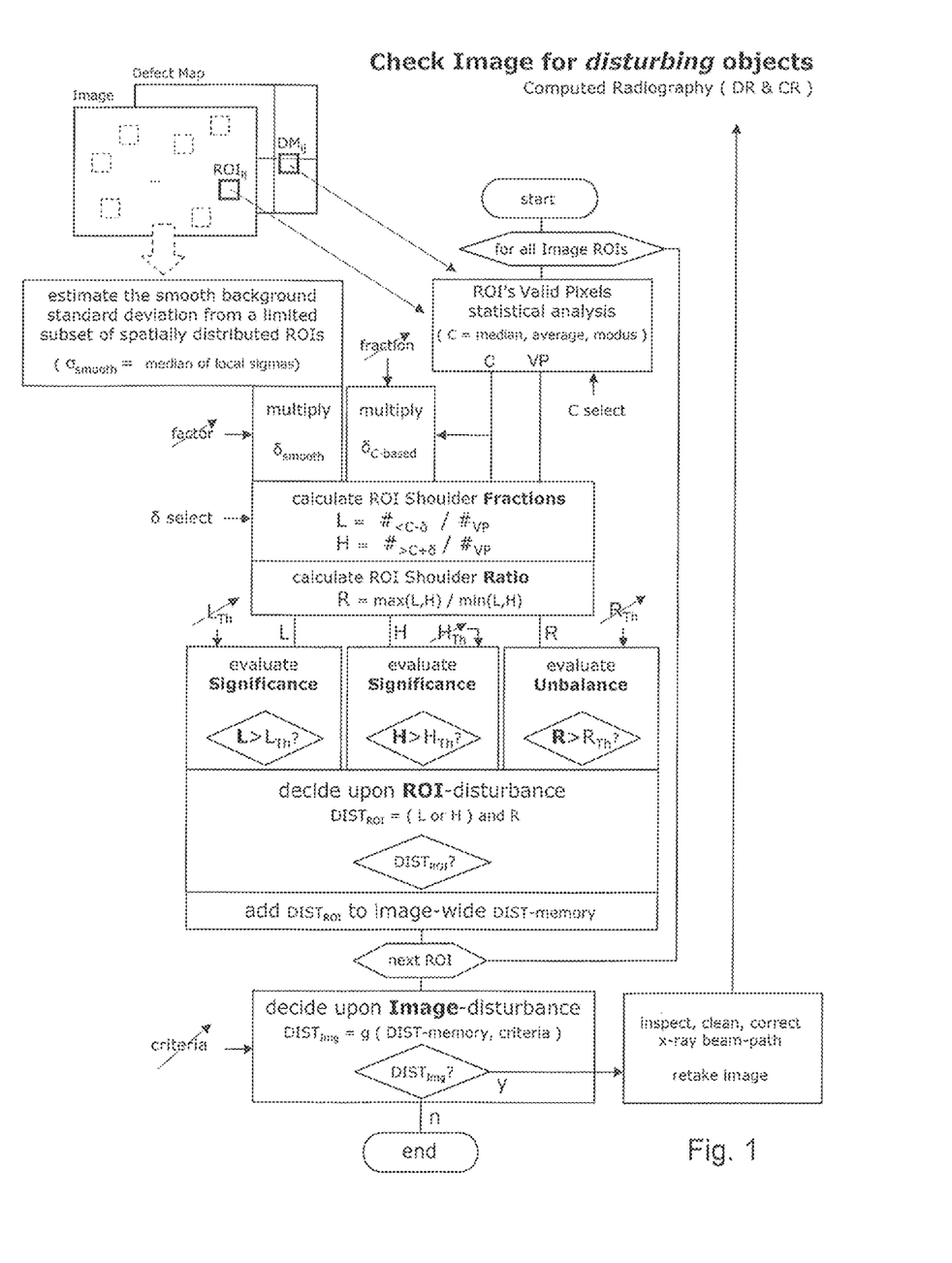
FIG. 1 illustrates the decision making logic based on the set of local shoulder significance and unbalance results analyzed in the image as compared to a set of predetermined threshold levels.

FIG. 1 explains a specific preferred embodiment of the method of this invention by a process flow-chart acting on an individual image, acquired for the purpose of gain map determination, which might contain a disturbed, local region-of-interest.

Figure 2:
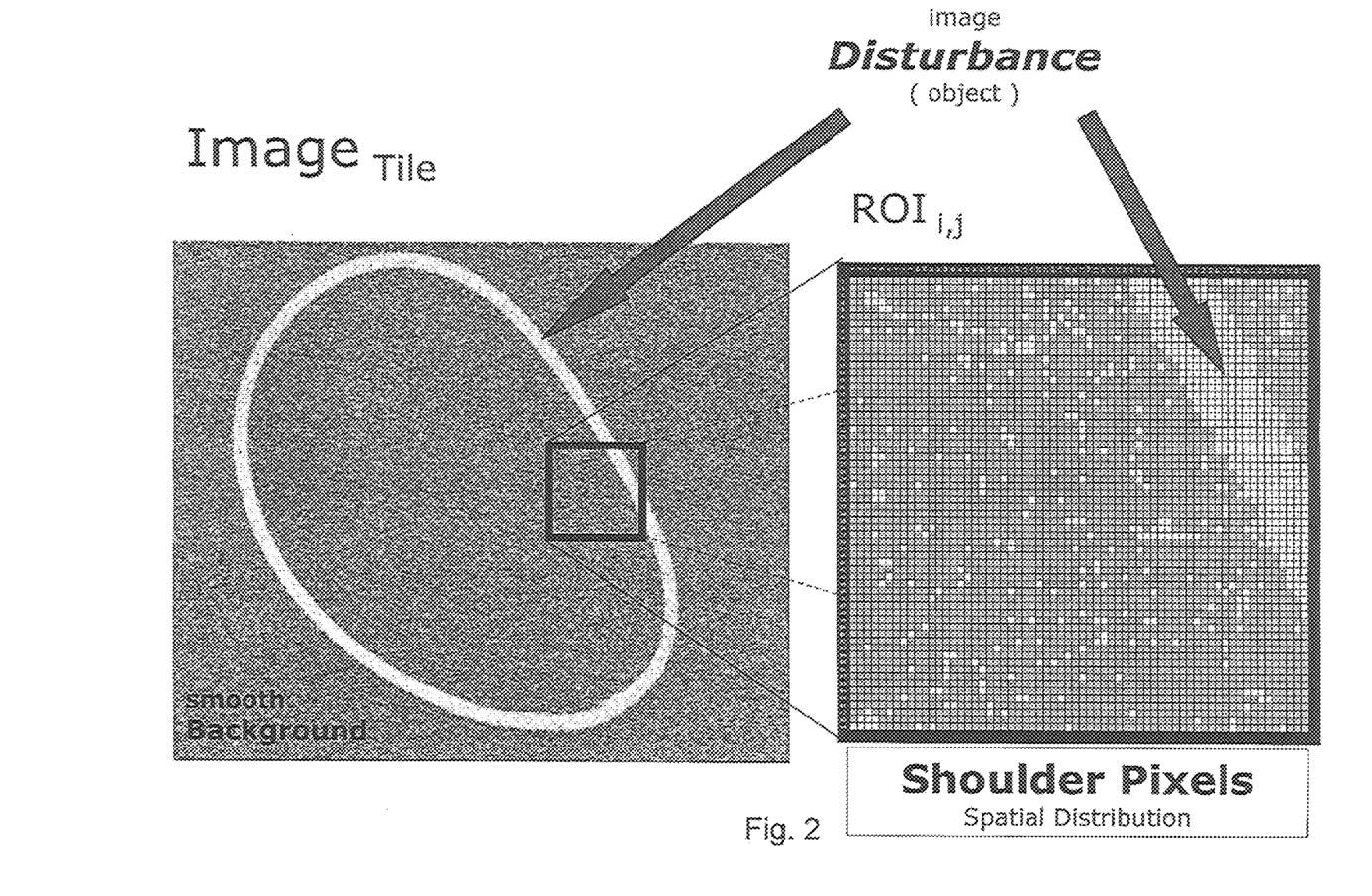
FIG. 2 represents a local region-of-interest as cropped from an object-disturbed image-tile and its statistical translation into spatially distributed shoulder-pixel patterns.

The avoidable, disturbed x-ray beam path condition is in this exemplary preferred embodiment caused by an elastic band which was left behind by accident on the detector-surface before starting with calibration-dedicated image acquisitions. This is depicted in FIG. 2.

A disturbed image-tile, represented with high contrast-magnification for improved visibility of this low x-ray absorption object, shows how this 'forgotten to remove' object partially intersects with an arbitrarily chosen region-of-interest ROIij and how it locally influences the normally expected smooth background noise pattern which is typical for a homogeneously exposed detector image.

The process of automatic detection of disturbing objects in homogeneously exposed flat field images starts by dividing the image, subjected to this inspection, in a plurality of much smaller, local regions-of-interest.

Although exactly adjacent local inspection ROIs minimize the inspection work, a partial overlap of neighbouring ROIs will be more effective for the detection of small, disturbing beam-path objects.

If these occur at the edge or in the corner of a local ROI the small size objects are sub-divided into even smaller image-disturbances scattered across the adjacent ROIs.

The bigger the ROI-overlap, the smaller the effect of spatial scattering across the neighbour ROIs will be.

The beam path inspection concept described in this preferred embodiment uses 64×64 pixels (8 mm square) inspection-ROIs with a ¼th ROI-size overlap in both image directions.

By consequence the entire image-impact caused by disturbing objects with lengths below 4 mm will thus always have its full effect either locally or in one of the eight partially overlapping, neighbour ROIs which are all subjected to this inspection too.

Once the image's inspection area is divided into a grid of partially overlapping inspection ROIs each of these local ROIs is analyzed as shown by the loop-structure in the FIG. 1 inspection method flowchart.

For direct radiography flat-panel detector imagery a predetermined so-called defect map which flags the detector-array's unreliable pixels, rows and columns may be available for the purpose of image-reconstruction using neighbouring, reliable pixel data.

Using that defect map (optionally), the inspection-ROI's valid pixels subset is derived from which either the local median (in a preferred embodiment) or the average or modus signal value is calculated.

Figure 3:
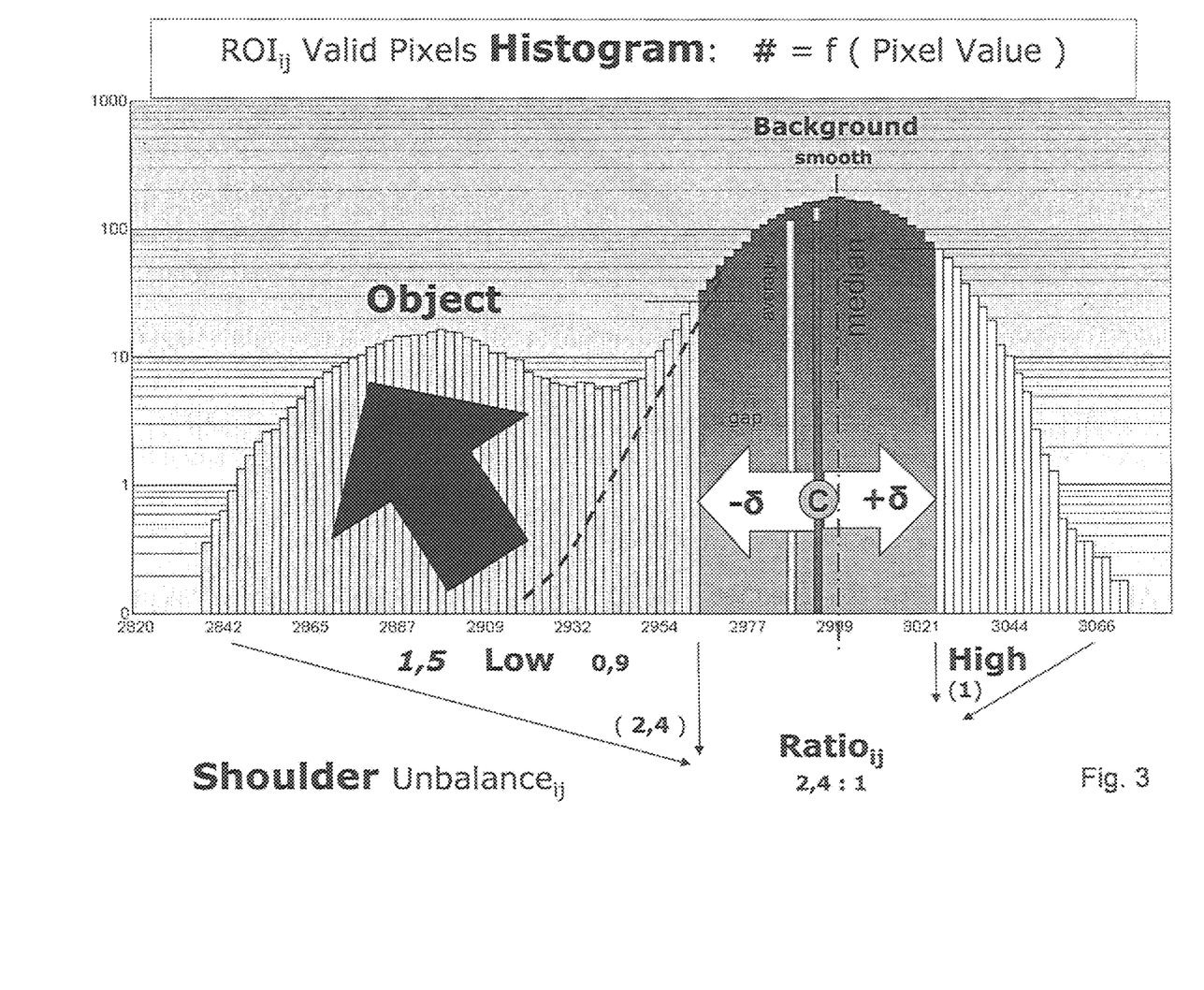
FIG. 3 represents the valid pixel histogram of the object-disturbed local region-of-interest as analyzed and split statistically into distinctly gap-separated lower and higher shoulder bins.

That value represents the central signal value "C" for the further operations performed on the histogram of valid pixel values as depicted in FIG. 3.

Since all the image-pixels are valid in digitizer-/media-based computed radiography (CR) a defect map is neither available nor required for the detection of beam-path disturbing objects during the inspection of the homogeneously exposed images made for the calculation of the CR-cassette's gain-image.

The histogram of undisturbed image-noise, as present in the smooth background signal of FIG. 2, is quantum noise dominated and is depicted as the dashed Gaussian-like distribution centred about the central value C in FIG. 3.

The image impact of a local object disturbance in the inspection ROI introduces x-ray absorption which reduces the signal values of the affected pixels in a way that the histogram becomes asymmetrical with respect to the vertical dash-dot line, representing the central signal value without the presence of that disturbing object.

The higher the object's absorption level, the lower the average signal value of the outward bulking lower signal shoulder.

The higher the amount of ROI pixels affected by the object, the bigger that secondary maximum of the local histogram.

Let's consider the lower and the higher signal values: C-delta and C+delta, symmetrically centered about the central signal value.

Assuming +/−1% C signal-value gaps, relative to the central signal value, a lower and a higher signal shoulder can be defined inside the local histogram as the collections of the lower and the higher valid pixel shoulder fractions composed of the spatially distributed pixels having signal-values below C-delta or above C+delta.

These shoulders can be expressed as fractions of the local ROI's valid pixels subset.

From the Shoulder Pixels Spatial Distribution view in FIG. 2, it can be seen that (for this image and with this +/−1% C delta) nearly equal amounts of about spatially evenly distributed pixels in the smooth background noise still belong to the low and the high histogram shoulders.

Seen from the pixel positions where the beam-path disturbing elastic band object is intersecting with the local inspection ROI however it is clear that these disturbed valid pixels all belong to the low histogram shoulder.

The histogram-gap, determined by the signal delta, that separates the low and the high shoulders from the central value can be predetermined as either a fraction of the central value itself or as a predetermined factor times the standard deviation of the smooth background noise, calculated as the median noise deviation estimate from a limited set of spatially distributed image ROIs.

This way the C-centered signal-gap separating both histogram-shoulders can automatically adapt itself to the amount of smooth background-noise present in the image under inspection.

Many experiments conducted on homogeneously exposed images with various types of disturbing objects in the beam path have shown that the combination of a sufficient level of unbalance between the local histogram's low and high shoulder fractions with a sufficient level of significance of at least one of both shoulder fractions is a sensitive, reliable and fast indicator for the presence of a disturbing object condition in the image under inspection.

The ROI's low and high shoulder fractions L and H are calculated as the amount of valid pixels with signals below the C-delta or above the C+delta value divided by the total amount of valid pixels locally present.

The shoulder ratio is calculated by dividing the biggest of both shoulder fractions by the smallest. Undisturbed image noise will typically return a near equity shoulder ratio.

Figure 4:
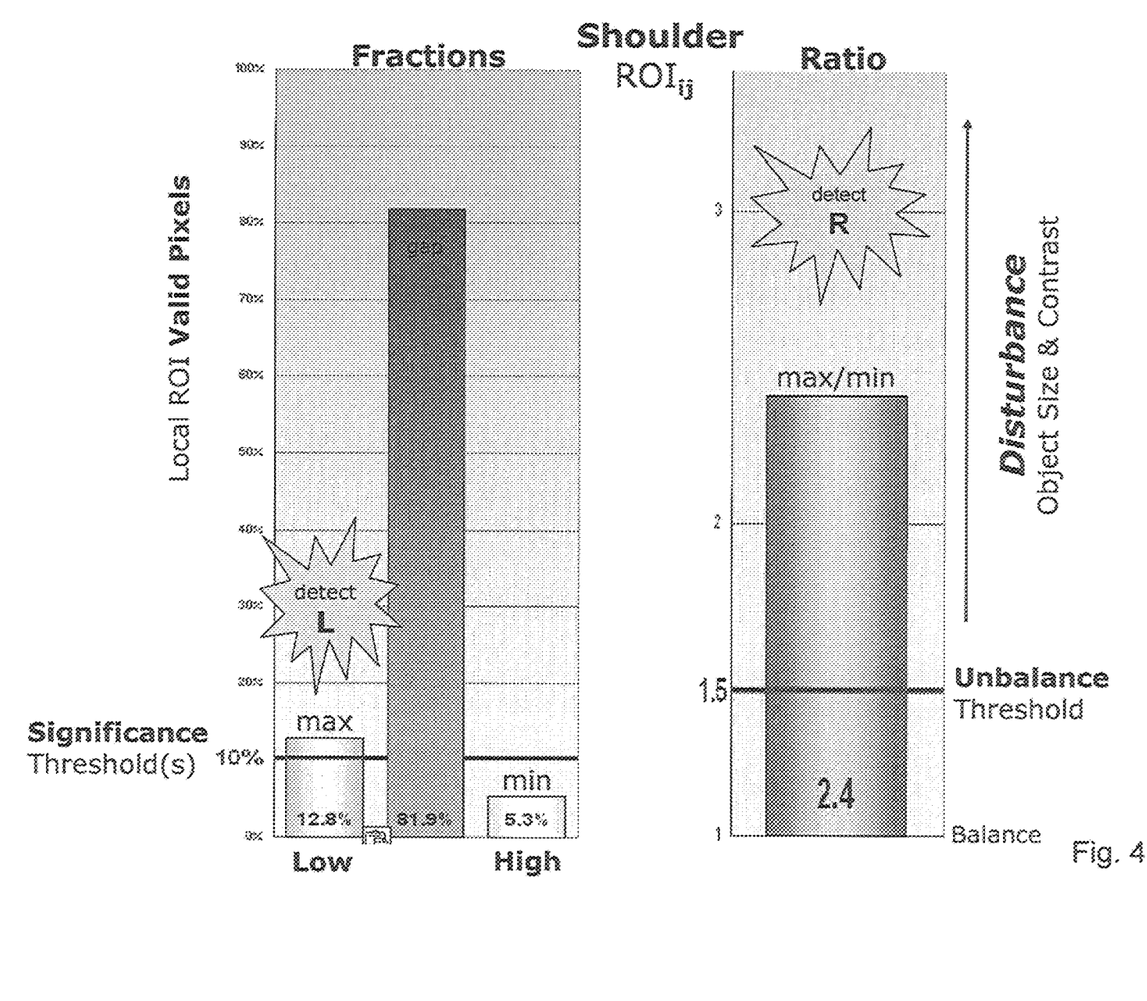
FIG. 4 represents both local shoulder fractions and their shoulder ratio relative to their significance and unbalance threshold levels.

The results of these calculations are shown in FIG. 4.

As soon as an object will generate an unbalance of the shoulder fractions, the shoulder ratio will increase Once the L and H shoulder fractions and their ratio R are locally calculated, each of them is compared to its predetermined threshold level.

The threshold for the shoulder fraction determines if the measured value is sufficiently significant to be flagged as one of the prerequisites for object detection.

The threshold for the shoulder ratio determines if the measured value is sufficiently unbalanced to be flagged as one of the prerequisites for object detection.

The decision logic for the detection of a ROI-disturbance is such that a local ROI is regarded as object-disturbed if a sufficient level of shoulder unbalance is present and if at the same time at least one shoulder fraction is sufficiently significant.

The result of that local ROI decision can be stored in an image-wide disturbance memory for further decision making regarding the image-disturbance at a higher level.

In case the detection of a single ROI-disturbance would be sufficient to regard the entire image as disturbed the further looping through the other inspection ROIs can be skipped.

Once all the local ROIs have been investigated and their logical disturbance status is known the decision about the object disturbance of the entire image is made by comparing the predetermined criteria with the content of the image-wide disturbance memory.

An image-wide criterion could be that a very limited amount of solitary disturbed ROIs can still be accepted if these isolated disturbances all occur in ROI's adjacent to the image borders.

If these criteria aren't fulfilled the investigation of the image is halted and the inspected image is accepted and added to the set of input-images for the purpose of system (re-)calibration.

If the image-wide disturbance criteria are met the beam path is regarded as object disturbed. In that case additional inspection, cleaning and or a correction (e.g. the removal of the disturbing object) of the x-ray beam path might be necessary before an image-retake can be performed.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A method to generate gain correction data for correcting a direct radiography or computed radiography image, the method comprising the steps of:
   exposing an x-ray detector to a substantially uniform x-ray beam to generate an x-ray image;
   converting the x-ray image into a digital image representation;
   using the digital image representation for calculation of the gain correction data;
   performing a statistical analysis on pixel values of at least one region of interest in the digital image representation;
   determining a presence of a source of x-ray beam inhomogeneity by comparing results of the statistical analysis with least one predetermined acceptance criterion; and
   using the digital image representation for the calculation of the gain correction data when it is determined in the determining step that no source of x-ray beam inhomogeneity is present; wherein
   the statistical analysis includes an evaluation of low and high histogram shoulders of a histogram of the pixel values in the region of interest determined relative to a center value in the histogram;
   the center value is a median, an average, or a modus value of the pixel values of the region of interest; and
   the method further comprises the step of determining a cause of the beam inhomogeneity by evaluating at least one significance level being determined by thresholding low and high shoulder fractions, the low and high shoulder fractions being determined as an amount of ROI-pixels with values below a low shoulder value divided by a total amount of ROI-pixels and an amount of ROI-pixels with values above a high shoulder value divided by the total amount of ROI-pixels.

2. The method according to claim 1, wherein at least two partially overlapping regions-of-interest are subjected to the statistical analysis.

3. The method according to claim 1, wherein a single region of interest is subjected to the statistical analysis.

4. The method according to claim 1, wherein the criterion is an image-wide criterion.

5. The method according to claim 1, wherein the statistical analysis is only performed on non-defective pixels in the at least one region of interest.

6. The method according to claim 1, wherein the low and high shoulder values are determined as the center value, the average, or the modus value minus and plus a predetermined fraction of:

the center value; or a median or an average of standard deviations calculated for a subset of spatially distributed regions-of-interest in the digital image representation.

7. The method according to claim 1, further comprising determining a cause of the beam inhomogeneity by performing a logical operation on at least one significance level and an unbalance level.

8. A method of subjecting a non-corrected detector-image, an offset-map corrected image, a defective-pixel-map corrected image, or a combination of both the offset-map corrected image and the defective-pixel-map corrected image to the method of claim 1.

9. A method to generate gain correction data for correcting a direct radiography or computed radiography image, the method comprising the steps of:

exposing an x-ray detector to a substantially uniform x-ray beam to generate an x-ray image;

converting the x-ray image into a digital image representation;

using the digital image representation for calculation of the gain correction data;

performing a statistical analysis on pixel values of at least one region of interest in the digital image representation;

determining a presence of a source of x-ray beam inhomogeneity by comparing results of the statistical analysis with least one predetermined acceptance criterion; and using the digital image representation for the calculation of the gain correction data when it is determined in the determining step that no source of x-ray beam inhomogeneity is present; wherein the statistical analysis includes an evaluation of low and high histogram shoulders of a histogram of the pixel values in the region of interest determined relative to a center value in the histogram;

the center value is a median, an average, or a modus value of the pixel values of the region of interest; and the method further comprises the step of determining a cause of the beam inhomogeneity by evaluating an unbalance level of a shoulder ratio relative to a predetermined ratio-threshold level, the shoulder ratio being determined as a largest shoulder fraction divided by a smallest shoulder fraction, and the low and high shoulder fractions are an amount of ROI-pixels with values below a low shoulder value and an amount of ROI-pixels with values above a high shoulder value.

10. The method according to claim 9, wherein at least two partially overlapping regions-of-interest are subjected to the statistical analysis.

11. The method according to claim 9, wherein a single region of interest is subjected to the statistical analysis.

12. The method according to claim 9, wherein the criterion is an image-wide criterion.

13. The method according to claim 9, wherein the statistical analysis is only performed on non-defective pixels in the at least one region of interest.

14. The method according to claim 9, wherein the low and high shoulder values are determined as the center value, the average, or the modus value minus and plus a predetermined fraction of:

the center value; or a median or an average of standard deviations calculated for a subset of spatially distributed regions-of-interest in the digital image representation.

15. The method according to claim 9, further comprising determining a cause of the beam inhomogeneity by performing a logical operation on at least one significance level and an unbalance level.

16. A method of subjecting a non-corrected detector-image, an offset-map corrected image, a defective-pixel-map corrected image, or a combination of both the offset-map corrected image and the defective-pixel-map corrected image to the method of claim 9.

* * * * *